(12) United States Patent
Wickham

(10) Patent No.: US 9,782,270 B2
(45) Date of Patent: Oct. 10, 2017

(54) SPINAL IMPLANT SYSTEM AND METHOD

(71) Applicant: Warsaw Orthopedic, Inc., Warsaw, IN (US)

(72) Inventor: Jeffrey Wickham, Hernando, MS (US)

(73) Assignee: Warsaw Orthopedic, Inc., Warsaw, IN (US)

(*) Notice: Subject to any disclaimer, the term of this patent is extended or adjusted under 35 U.S.C. 154(b) by 413 days.

(21) Appl. No.: 14/454,868

(22) Filed: Aug. 8, 2014

(65) Prior Publication Data

US 2016/0038301 A1 Feb. 11, 2016

(51) Int. Cl.
*A61F 2/44* (2006.01)
*A61F 2/30* (2006.01)

(52) U.S. Cl.
CPC ............ *A61F 2/447* (2013.01); *A61F 2/4455* (2013.01); *A61F 2002/30011* (2013.01); *A61F 2002/30028* (2013.01); *A61F 2002/30029* (2013.01); *A61F 2002/3092* (2013.01); *A61F 2002/3093* (2013.01); *A61F 2002/30774* (2013.01); *A61F 2002/30904* (2013.01); *A61F 2002/30971* (2013.01); *A61F 2002/4475* (2013.01); *A61F 2310/00023* (2013.01)

(58) Field of Classification Search
CPC .................................. A61F 2/447; A61F 2/44
USPC .......................................... 623/17.11–17.16
See application file for complete search history.

(56) References Cited

U.S. PATENT DOCUMENTS

| | | | | |
|---|---|---|---|---|
| 4,834,757 A * | 5/1989 | Brantigan | ............ | A61B 17/1604 623/17.11 |
| 4,911,718 A * | 3/1990 | Lee | ............ | A61F 2/442 623/17.15 |
| 4,932,969 A * | 6/1990 | Frey | ............ | A61F 2/441 623/17.12 |
| 5,047,055 A * | 9/1991 | Bao | ............ | A61F 2/441 623/17.16 |
| 5,171,281 A * | 12/1992 | Parsons | ............ | A61F 2/442 623/17.15 |
| 5,674,294 A * | 10/1997 | Bainville | ............ | A61F 2/442 623/17.16 |
| 6,113,639 A * | 9/2000 | Ray | ............ | A61F 2/4684 623/17.16 |
| 6,402,784 B1 * | 6/2002 | Wardlaw | ............ | A61B 17/8891 623/17.11 |
| 6,533,818 B1 * | 3/2003 | Weber | ............ | A61F 2/441 623/17.16 |
| 6,733,533 B1 * | 5/2004 | Lozier | ............ | A61F 2/441 606/247 |
| 6,958,077 B2 * | 10/2005 | Suddaby | ............ | A61F 2/441 623/17.11 |
| 6,966,931 B2 * | 11/2005 | Huang | ............ | A61F 2/4425 623/17.11 |
| 6,984,246 B2 * | 1/2006 | Huang | ............ | A61F 2/441 623/17.12 |
| 7,001,431 B2 * | 2/2006 | Bao | ............ | A61B 17/7097 606/247 |
| 7,169,181 B2 * | 1/2007 | Kuras | ............ | A61F 2/442 623/17.11 |

(Continued)

*Primary Examiner* — David Bates

(57) ABSTRACT

A spinal implant comprises a first vertebral engaging surface and a second vertebral engaging surface. A wall extends between the surfaces. The wall includes an inner bone growth resistant layer and an outer layer. Systems and methods of use are disclosed.

20 Claims, 3 Drawing Sheets

(56) References Cited

U.S. PATENT DOCUMENTS

| | | | | |
|---|---|---|---|---|
| 7,441,559 B2 * | 10/2008 | Nelson | | A61F 2/00 128/848 |
| 7,563,284 B2 * | 7/2009 | Coppes | | A61F 2/441 623/17.12 |
| 7,691,130 B2 * | 4/2010 | Bruneau | | A61B 17/7062 606/249 |
| 7,776,092 B2 * | 8/2010 | Lee | | A61F 2/0811 623/17.13 |
| 7,910,124 B2 * | 3/2011 | Boyan | | A61F 2/442 424/424 |
| 8,038,718 B2 * | 10/2011 | Palm | | A61F 2/442 623/17.16 |
| 8,092,542 B2 * | 1/2012 | Bryan | | A61B 17/02 623/16.11 |
| 8,167,945 B1 * | 5/2012 | Castro | | A61F 2/442 606/246 |
| 8,403,987 B2 * | 3/2013 | Reo | | A61F 2/441 623/17.11 |
| 8,470,040 B2 * | 6/2013 | Kovarik | | A61F 2/447 623/17.11 |
| 8,556,981 B2 * | 10/2013 | Jones | | A61F 2/30907 623/18.11 |
| 8,636,803 B2 * | 1/2014 | Hibri | | A61F 2/441 623/17.12 |
| 2003/0055506 A1 * | 3/2003 | Stoy | | A61F 2/441 623/17.16 |
| 2004/0133279 A1 * | 7/2004 | Krueger | | A61B 17/7062 623/17.16 |
| 2005/0015154 A1 * | 1/2005 | Lindsey | | A61B 17/68 623/23.46 |
| 2005/0065609 A1 * | 3/2005 | Wardlaw | | A61F 2/441 623/17.12 |
| 2006/0173542 A1 * | 8/2006 | Shikinami | | A61F 2/30965 623/14.12 |
| 2006/0195191 A1 * | 8/2006 | Sweeney, II | | A61F 2/442 623/17.13 |
| 2007/0179611 A1 * | 8/2007 | DiPoto | | A61F 2/442 623/17.11 |
| 2008/0161920 A1 | 7/2008 | Melkent | | |
| 2009/0118836 A1 | 5/2009 | Cordaro | | |
| 2011/0029087 A1 | 2/2011 | Haider | | |
| 2011/0071635 A1 * | 3/2011 | Zhang | | B32B 15/08 623/17.11 |
| 2011/0224796 A1 | 9/2011 | Weiland et al. | | |
| 2016/0022430 A1 * | 1/2016 | Wickham | | A61F 2/447 623/17.16 |

\* cited by examiner

SPINAL IMPLANT SYSTEM AND METHOD

TECHNICAL FIELD

The present disclosure generally relates to medical devices for the treatment of musculoskeletal disorders, and more particularly to a surgical system and method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods and interbody devices can be used to provide stability to a treated region. For example, during surgical treatment, interbody implants can be delivered to a surgical site for fixation with bone to immobilize a joint. This disclosure describes an improvement over these prior art technologies.

SUMMARY

In one embodiment, a spinal implant is provided that comprises a first vertebral engaging surface and a second vertebral engaging surface. A wall extends between the surfaces. The wall includes an inner bone growth resistant layer and an outer layer. In some embodiments, systems and methods are provided.

BRIEF DESCRIPTION OF THE DRAWINGS

The present disclosure will become more readily apparent from the specific description accompanied by the following drawings, in which.

DETAILED DESCRIPTION

Figure 1:
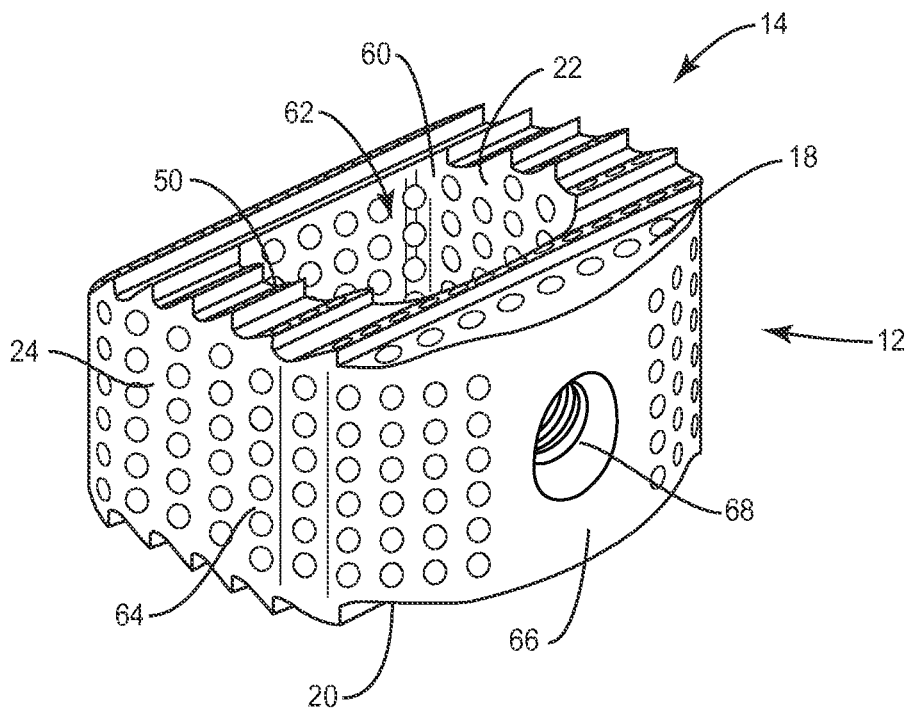
FIG. 1 is a perspective view of components of one embodiment of a system in accordance with the principles of the present disclosure.

The exemplary embodiments of the surgical system and related methods of use disclosed are discussed in terms of medical devices for the treatment of musculoskeletal disorders and more particularly, in terms of a surgical system including a spinal implant and a method for treating a spine. In one embodiment, the systems and methods of the present disclosure are employed with a spinal joint fusion, for example, with a cervical, thoracic, lumbar and/or sacral region of a spine. In one embodiment, the spinal implant includes an interbody device, a plate and/or bone fasteners.

In some embodiments, the present system comprises a spinal implant including a titanium interbody spacer with a modulus of elasticity of bone. In some embodiments, the spinal implant includes an interbody spacer having an open porous layer, a solid layer for sealing and an inner porous core. In some embodiments, the spinal implant minimizes stress shielding. In some embodiments, the spinal implant has a porous structure that allows bone to grow into the implant and mechanically lock it in place. In some embodiments, the spinal implant provides a reduced modulus while offering a bone ingrowth feature.

In some embodiments, the spinal implant includes an interbody spacer with an open porous outer layer combined with a sealed porous inner core. In some embodiments, the spinal implant facilitates bony ingrowth on a thin outer layer to mechanically lock the implant and bone together. In some embodiments, the spinal implant includes a sealed porous inner layer that reduces the modulus and does not allow bony ingrowth to subsequently stiffen a lattice of the implant.

In some embodiments, the present spinal implant can be manufactured employing additive manufacturing technology such as electron beam manufacturing or direct metal laser sintering. In some embodiments, the present spinal implant can be manufactured through multi-shot metal injection molding using a space-holder method.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

Figure 2:
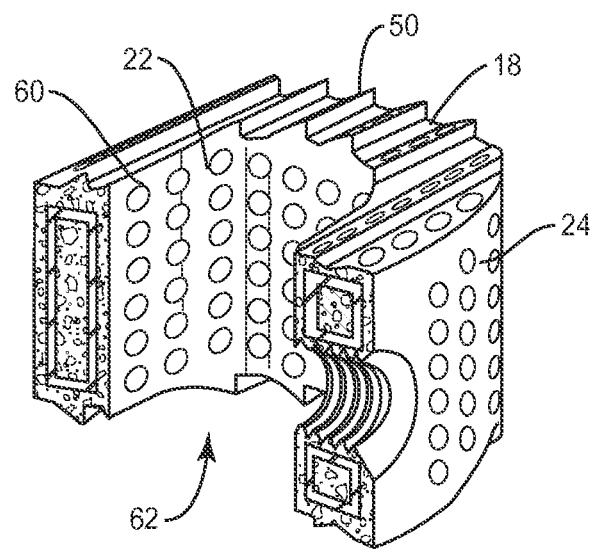
FIG. 2 is a cutaway view of the components shown in FIG. 1.
Figure 3:
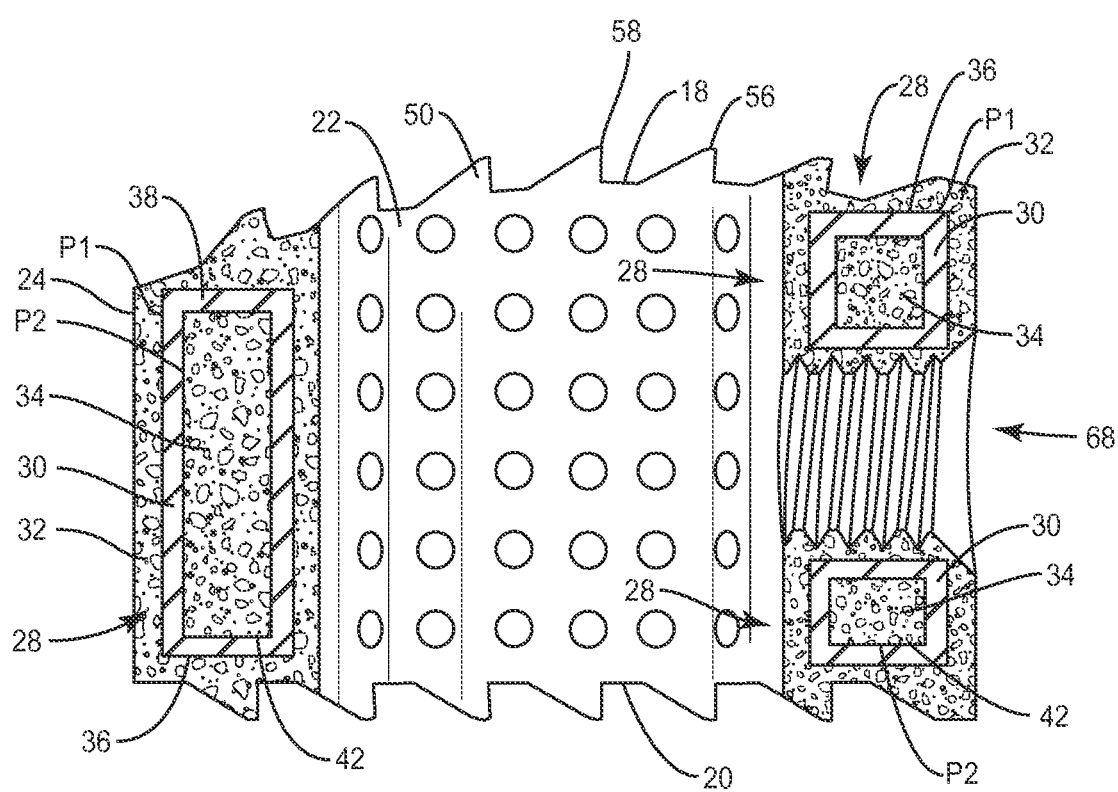
FIG. 3 is a cross section view of the components shown in FIG. 1.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-3, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, rnorselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein. In one embodiment, a spinal implant, as described herein, may be formed substantially of a biocompatible metal, such as titanium and selectively coated with a bone-growth promoting material, such as HA. In one embodiment, a spinal implant, as described herein, may be formed substantially of a biocompatible polymer, such as PEEK, and selectively coated with a biocompatible metal, such as titanium, or a bone-growth promoting material, such as HA. In some embodiments, titanium may be plasma sprayed onto surfaces of the spinal implant to modify a radiographic signature of the spinal implant and/or improve bony ongrowth to the spinal implant by application of a porous or semi-porous coating of titanium.

Spinal implant system 10 may be employed, for example, with minimally invasive procedures, including percutaneous techniques, mini-open surgical techniques and/or open surgical techniques to deliver and introduce instrumentation and/or implants, such as, for example, an interbody implant, at a surgical site within a subject body of a patient, which includes, for example, a spine. In some embodiments, the implant can include spinal constructs including one or more bone fasteners, spinal rods, connectors and/or plates. In some embodiments, various components of spinal implant system 10 may be utilized in open or traditional spinal surgical techniques.

Spinal implant system 10 includes an interbody implant 12. Interbody implant 12 has an implant body 14 that defines a longitudinal axis X1. Implant body 14 comprises a vertebral engaging surface 18 and a vertebral engaging surface 20. In some embodiments, the cross-section geometry of implant body 14 may have various configurations, such as, for example, cylindrical, oval, oblong, triangular, polygonal having planar or arcuate side portions, irregular, uniform, non-uniform, consistent, variable, horseshoe shape, U-shape or kidney bean shape. In some embodiments, surface 18 and/or surface 20 may be rough, textured, porous, semi-porous, dimpled, knurled, toothed, grooved and/or polished to facilitate engagement with tissue. In some embodiments, the vertebral tissue may include intervertebral tissue, endplate surfaces and/or cortical bone. In some embodiments, all or only a portion of interbody implant 12 includes, is fabricated from and/or is coated with titanium.

Implant body 14 includes an inner wall 22 that extends between surfaces 18, 20. Implant body 14 includes an outer wall 24 that extends between surfaces 18, 20. Walls 22, 24 are spaced apart between surfaces 18, 20 for disposal of a stratum 28, as described herein. In some embodiments, wall 22 and/or wall 24 may be rough, textured, porous, semi-porous, dimpled, knurled, toothed, grooved and/or polished.

Stratum 28 is configured for disposal between walls 22, 24. In some embodiments, stratum 28 may include wall 22 and/or wall 24. Stratum 28 includes an inner core layer 34 disposed centrally relative to walls 22, 24. Layer 34 is porous and/or includes a plurality of openings. In some embodiments, this configuration of layer 34 reduces a modulus of elasticity and increases flexibility of implant body 14. An inner bone growth resistant layer 30 is disposed entirely about layer 34 to resist and/or prevent bony ingrowth of layer 34, as described herein. An outer layer 32 is disposed entirely about layer 30 and facilitates tissue and bony ingrowth with implant body 14, as described herein. In some embodiments, stratum 28 includes a core layer 34 that comprises an open space with layer 30 disposed entirely about the open space.

Layer 32 is entirely disposed about a surface 36 that defines a perimeter p1 of layer 30. In some embodiments, layer 32 completely surrounds perimeter p1 and includes a lattice 38 disposed thereabout. In some embodiments, lattice 38 has a porous configuration and/or includes a plurality of openings that facilitate tissue and bony ingrowth with implant body 14. In some embodiments, layer 32 and/or lattice 38 are configured for disposal of tissue and/or other bone growth promoting material, which may include osteogenic tissue, to create a mechanical interlock of implant body 14 of interbody implant 12 with a vertebral endplate and/or form a scaffold for bone growth to facilitate fixation and fusion.

In some embodiments, lattice 38 may include one or more portions, layers and/or substrates disposed in a side by side, offset, staggered, stepped, tapered, end to end, spaced apart, series and/or parallel orientation. In some embodiments, lattice 38 defines a thickness, which may be uniform, undulating, tapered, increasing, decreasing, variable, offset, stepped, arcuate, angled and/or staggered. In one embodiment, lattice 38 includes titanium, as described herein.

Surface 36 is disposed adjacent and in contacting engagement with an inner surface of layer 30. Surface 36 has a continuous and uninterrupted configuration that resists and/or prevents bony ingrowth of layer 34. As such, layer 30 seals inner core layer 34 from bony ingrowth facilitated by layer 32. In some embodiments, at least a portion of layer 30 is solid. In some embodiments, stratum 28 does not include a layer 34 such that layer 30 is disposed entirely about and seals an open space or cavity from bony ingrowth facilitated by layer 32.

Core layer 34 includes a surface 42 that defines a perimeter p2 of layer 34. An inner surface of layer 30 is disposed adjacent and in contacting engagement with surface 42. The inner surface of layer 30 has a continuous and uninterrupted configuration that resists and/or prevents bony ingrowth into layer 34 and/or migration of bony ingrowth facilitated by layer 32. In some embodiments, layer 30 is disposed about perimeter p2 to form a seal between core layer 34 and layer 32 such that bone ingrowth to layer 34 is resisted and/or prevented. In some embodiments, this configuration of layers 30, 32, 34 maintains a reduced modulus of elasticity and increased flexibility of implant body 14.

In some embodiments, stratum 28 provides a modulus of elasticity to implant body 14 in a range of the modulus of bone. In some embodiments, implant body 14 has a modulus of elasticity in a range of approximately 300 MPa to approximately 12000 MPa.

In some embodiments, stratum 28 may include one or a plurality of layers. In some embodiments, the layers of stratum 28 may be partially, circumferentially or entirely disposed about an adjacent layer. In some embodiments, one or more layers of stratum 28 may be disposed in a relative orientation, such as, for example, side by side, parallel, perpendicular, angled, collectively angled relative to implant body 14, converging, diverging, staggered, offset. In some embodiments, one or more layers of stratum 28 may be fabricated from the same or different materials, as described herein. In some embodiments, one or more layers of stratum 28 may include the same or different porosity, modulus of elasticity, rigidity and/or hardness. In some embodiments, one or more layers of stratum 28 may define various cross section configurations, such as, for example, cylindrical, oval, oblong, triangular, polygonal having planar or arcuate side portions, irregular, uniform, non-uniform, consistent, variable, horseshoe shape, U-shape or kidney bean shape. In some embodiments, stratum 28 and/or one or more layers of stratum 28 may define a thickness, which may be uniform, undulating, tapered, increasing, decreasing, variable, offset, stepped, arcuate, angled and/or staggered.

In some embodiments, implant body 14 includes a tissue penetrating member, such as, for example, a tooth 50 disposed transversely along surface 18 and/or surface 20, as shown in FIG. 1. In some embodiments, implant body 14 includes a plurality of teeth 50. In some embodiments, one or more teeth 50 may have various configurations, for example, parallel, converging, diverging, irregular, tapered, offset, staggered, uniform and non-uniform.

Each tooth 50 includes a cutting surface 56 configured to engage endplate tissue, such as, for example, soft tissues, bone and/or fluids to cut, shave, shear, incise and/or remove such tissue. Surface 56 includes a cutting tip, such as, for example, a solid cutting tip 58. In one embodiment, each tooth 50 includes a surface that defines at least one opening. In some embodiments, one or more the openings are configured to form a porous tooth surface adjacent tip 58.

In some embodiments, teeth 50 may be disposed in a serial and/or overlapping configuration to provide a matrix of teeth 50. In some embodiments, teeth 50 are disposed along surface 18 and/or surface 20 such that cut osteogenic tissue and/or other bone growth promoting material create a mechanical interlock of implant body 14 with a vertebral endplate and/or form a scaffold for bone growth. Wall 22 includes a surface 60 that defines an opening, such as, for example, an axial opening 62 configured to receive an agent, which may include bone graft (not shown) and/or other materials, as described herein, for employment in a fixation or fusion treatment.

Well 24 includes continuous and uninterrupted lateral faces 64. In some embodiments, face 64 is solid and configured for disposal of visual indicia. In one embodiment, the visual indicia is configured to provide configuration and/or a dimension of interbody implant 12. In one embodiment, a face 66 includes an opening 68 configured to facilitate engagement with a surgical tool or instrument for positioning and alignment of interbody implant 12 with tissue, as described herein. In some embodiments, system 10 may comprise a kit including a plurality of implants with visual indicia indicative of their respective configuration and dimension. In some embodiments, the visual indicia may include color coding to provide configuration and/or a dimension of interbody implant 12.

Figure 4:
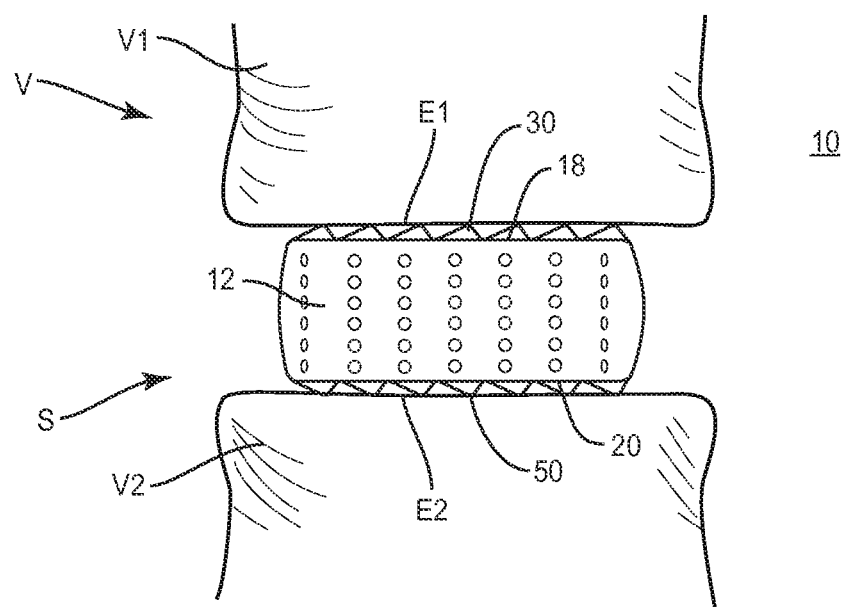
FIG. 4 is a side view of the components shown in FIG. 1 disposed with vertebrae.

In assembly, operation and use, as shown in FIG. 4, spinal implant system 10, similar to the systems and methods described herein, is disposed with tissue, such as, for example, vertebrae V for treatment of a spinal disorder, such as those described herein, affecting a section of a spine of a patient. Spinal implant system 10 may also be employed with other surgical procedures.

To treat the affected section of vertebrae V, an incision is made with a surgical instrument, such as, for example, a scalpel. In some embodiments, a discectomy is performed adjacent the intervertebral space. In some embodiments, sequential trial implants are delivered and used to distract the intervertebral space and apply appropriate tension in the intervertebral space allowing for indirect decompression. In some embodiments, the size of interbody implant 12 is selected after trialing. In some embodiments, interbody implant 12 is visualized by fluoroscopy and oriented before malleting into the intervertebral space.

An inserter (not shown) is connected with interbody implant 12 via opening 68 to direct interbody implant 12 between vertebrae V1, V2 such that surface 18 is disposed in a cephalad orientation of the body and surface 20 is disposed in a caudal orientation of the body. The inserter delivers interbody implant 12 through the incision to a surgical site for implantation into the intervertebral space S between vertebrae V1, V2.

As interbody implant 12 is inserted into space S, teeth 50 translate along the surface of endplate E1 and/or endplate E2. Translation of teeth 50 along the surfaces of endplate E1 and/or endplate E2 cause teeth 50 and/or surfaces 18, 20 to engage the soft tissues, bone and/or fluids of endplate E1 and/or endplate E2 for forming a mechanical lock of interbody implant 12 with vertebrae V1, V2. In an implanted position, as shown in FIG. 4, surface 18 engages endplate tissue of endplate E1 and surface 20 engages endplate tissue E2.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiopaque markers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of plates, connectors and/or bone fasteners for use with a single vertebral level or a plurality of vertebral levels.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
   a first vertebral engaging surface;
   a second vertebral engaging surface; and
   a wall extending between the surfaces, the wall including opposite inner and outer surfaces, the inner surface defining a cavity that extends through the first and second vertebral engaging surfaces, the wall comprising a stratum having a core layer disposed centrally relative to the inner and outer surfaces, an inner layer that encloses the core layer and an outer layer disposed about the inner layer, the inner layer forming a seal between the outer layer and the core layer to prevent bony ingrowth into the core layer.

2. A spinal implant as recited in claim 1, wherein at least a portion of the outer layer is porous.

3. A spinal implant as recited in claim 1, wherein the outer layer is disposed about a perimeter of the inner layer.

4. A spinal implant as recited in claim 1, wherein the outer layer is disposed entirely about the inner layer.

5. A spinal implant as recited in claim 1, wherein the outer layer comprises a lattice disposed about the inner layer.

6. A spinal implant as recited in claim 5, wherein the lattice includes a modulus of elasticity in a range of 300 to 12000 MPa.

7. A spinal implant as recited in claim 1, wherein at least a portion of the inner layer includes a continuous and uninterrupted surface.

8. A spinal implant as recited in claim 1, wherein at least a portion of the inner layer is solid.

9. A spinal implant as recited in claim 1, wherein the inner layer is disposed about at least a portion of the core layer.

10. A spinal implant as recited in claim 1, wherein at least a portion of the core layer is porous and includes a plurality of openings.

11. A spinal implant as recited in claim 1, wherein the inner layer is disposed about a perimeter of the core layer.

12. A spinal implant as recited in claim 1, wherein the outer layer is disposed about a perimeter of the inner layer and the inner layer is disposed about a perimeter of the core layer.

13. A spinal implant as recited in claim 1, wherein the spinal implant comprises an implant body including titanium.

14. A spinal implant as recited in claim 1, wherein at least one of the first and second vertebral engaging surfaces includes at least one tissue penetrating member.

15. A spinal implant as recited in claim 1, wherein at least one of the first and second vertebral engaging surfaces includes a plurality of teeth extending transversely thereoalong.

16. A spinal implant comprising:
    a first vertebral engaging surface;
    a second vertebral engaging surface; and
    a wall extending between the surfaces, the wall including opposite inner and outer surfaces, the inner surface defining a cavity that extends through the first and second vertebral engaging surfaces, the wall including a stratum comprising a core disposed centrally relative to the inner and outer surfaces, an inner layer that surrounds the core on all sides of the core and an outer layer disposed about the inner layer, the inner layer forming a seal between the outer layer and the core to prevent bony ingrowth into the core.

17. A spinal implant as recited in claim 16, wherein the outer layer comprises a titanium lattice.

18. A spinal implant comprising:
    a titanium body including a first vertebral engaging surface and a second vertebral engaging surface, the surfaces each including a plurality of tissue penetrating members engageable with a vertebral endplate; and
    a wall extending between the surfaces and including opposite inner and outer surfaces, the inner surface defining a cavity that extends through the first and second vertebral engaging surfaces, the wall including an outer lattice, an inner core and a solid layer disposed between the outer lattice and the inner core, the inner core being disposed centrally relative to the inner and outer surfaces, the solid layer enclosing the inner core such that the solid layer forms a seal between the outer lattice and the inner core to prevent bony ingrowth into the inner core, the wall including a threaded bore that extends through the inner and outer surfaces and is in communication with the cavity.

19. A spinal implant as recited in claim 1, wherein the core layer comprises an open space and the inner layer is disposed entirely about the open space.

20. A spinal implant as recited in claim 1, wherein the core does not extend through either of the first and second vertebral engaging surfaces.

\* \* \* \* \*

UNITED STATES PATENT AND TRADEMARK OFFICE
CERTIFICATE OF CORRECTION

PATENT NO. : 9,782,270 B2  
APPLICATION NO. : 14/454868  
DATED : October 10, 2017  
INVENTOR(S) : Wickham Page 1 of 1

It is certified that error appears in the above-identified patent and that said Letters Patent is hereby corrected as shown below:

In the Specification

In Column 1, Line 3, delete "HELD" and insert -- FIELD --, therefor.

In Column 3, Line 60, delete "tricalciurn" and insert -- tricalcium --, therefor.

In Column 3, Line 67, delete "rnorselized" and insert -- morselized --, therefor.

In Column 6, Line 47, delete "Well" and insert -- Wall --, therefor.

Signed and Sealed this  
Thirteenth Day of March, 2018

Andrei Iancu  
*Director of the United States Patent and Trademark Office*